US009297038B2

(12) United States Patent
Yang et al.

(10) Patent No.: US 9,297,038 B2
(45) Date of Patent: Mar. 29, 2016

(54) METHOD AND KIT FOR THE QUANTIFICATION OF NUCLEIC ACIDS

(75) Inventors: In Chul Yang, Daejeon (KR); Min Jung Kang, Daejeon (KR); Han Nah Yu, Daejeon (KR); Sang Ryoul Park, Daejeon (KR); Sook Kyoung Kim, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 227 days.

(21) Appl. No.: 13/989,729

(22) PCT Filed: Nov. 9, 2011

(86) PCT No.: PCT/KR2011/008494
§ 371 (c)(1),
(2), (4) Date: Jul. 1, 2013

(87) PCT Pub. No.: WO2012/070788
PCT Pub. Date: May 31, 2012

(65) Prior Publication Data
US 2013/0295577 A1   Nov. 7, 2013

(30) Foreign Application Priority Data

Nov. 25, 2010   (KR) .................... 10-2010-0118387

(51) Int. Cl.
*C12Q 1/68* (2006.01)
*C12P 19/34* (2006.01)

(52) U.S. Cl.
CPC ..................... *C12Q 1/686* (2013.01)

(58) Field of Classification Search
None
See application file for complete search history.

(56) References Cited

U.S. PATENT DOCUMENTS 6,432,650 B1 *   8/2002   Christian et al. ............. 435/6.14
2004/0209298 A1 * 10/2004   Kamberov et al. ............. 435/6

OTHER PUBLICATIONS

Feher et al., "Improved DOP-PCR—Based Representational Whole-Genome Amplification Using Quantitative Real-Time PCR," 2006, Diagn. Mol. Pathol., vol. 15, No. 1, pp. 43-48.
Korean Patent Office, Korean Grant Certification issued in corresponding KR Application No. 10-2010-0118387, issued on Aug. 22, 2013.
Kun Zhang, et al., "Sequencing genomes from single cells by polymerase cloning", Nature Biotechnology, May 28, 2006, pp. 680-686, vol. 24, No. 6.
Robert L. Green, et al., "Developmental Validation of the Quantifiler™ Real-Time PCR Kits for the Quantification of Human Nuclear DNA Samples", Journal of Forensic Science, Jul. 2005, pp. 1-17, vol. 50, No. 4.
T. Kuukasjarvi, et al., "Optimizing DOP-PCR for Universal Amplification of Small DNA Samples in Comparative Genomic Hybridization", Genes, Chromosomes & Cancer, Feb. 1997, pp. 94-101, vol. 18.
Qiang Huang, et al., "Improving Degenerate Oligonucleotide Primed PCR-Comparative Genomic Hybridization for Analysis of DNA Copy Number Changes in Tumors", Genes, Chromosomes & Cancer, Aug. 2000, pp. 395-403, vol. 28.
Sun-Hun Kim, et al., "Whole Genome Amplification and Molecular Genetic Analysis of DNA From Paraffin-Embedded Prostate Adenocarcinoma Tumor Tissue", Journal of Urology, Oct. 1999, pp. 1512-1518, vol. 162.
International Searching Authority, International Search Report, PCT/KR2011/008494, Jun. 22, 2012.

* cited by examiner

*Primary Examiner* — Kenneth R. Horlick
*Assistant Examiner* — David Thomas
(74) *Attorney, Agent, or Firm* — Sughrue Mion, PLLC

(57) ABSTRACT

Disclosed are a method and a kit for the quantification of nucleic acids, especially a trace amount of nucleic acid, such as host cell nucleic acid impurities, using real-time PCR with a random primer.

7 Claims, 5 Drawing Sheets

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial
<220> FEATURE:
<223> OTHER INFORMATION: Synthetic construct
<220> FEATURE:
<221> NAME/KEY: SITE
<222> LOCATION: (11)..(16)
<223> OTHER INFORMATION: n is a or g or c or t

<400> SEQUENCE: 1
ccgactcgag nnnnnnatgt gg                                          22

<210> SEQ ID NO 2
```

```
<211> LENGTH: 22
<212> TYPE: DNA
<213> ORGANISM: Artificial
<220> FEATURE:
<223> OTHER INFORMATION: Synthetic construct
<220> FEATURE:
<221> NAME/KEY: SITE
<222> LOCATION: (11)..(16)
<223> OTHER INFORMATION: n is a or g or c or t

<400> SEQUENCE: 2
ccgactcgag nnnnnnattt cg                                      22

<210> SEQ ID NO 3
<211> LENGTH: 22
<212> TYPE: DNA
<213> ORGANISM: Artificial
<220> FEATURE:
<223> OTHER INFORMATION: Synthetic construct
<220> FEATURE:
<221> NAME/KEY: SITE
<222> LOCATION: (11)..(16)
<223> OTHER INFORMATION: n is a or g or c or t

<400> SEQUENCE: 3
ccgactcgag nnnnnncggg tc                                      22

<210> SEQ ID NO 4
<211> LENGTH: 22
<212> TYPE: DNA
<213> ORGANISM: Artificial
<220> FEATURE:
<223> OTHER INFORMATION: Synthetic construct
<220> FEATURE:
<221> NAME/KEY: SITE
<222> LOCATION: (11)..(16)
<223> OTHER INFORMATION: n is a or g or c or t

<400> SEQUENCE: 4
ccgactcgag nnnnnntgtt cg                                      22

<210> SEQ ID NO 5
<211> LENGTH: 18
<212> TYPE: DNA
<213> ORGANISM: Artificial
<220> FEATURE:
<223> OTHER INFORMATION: Synthetic construct

<400> SEQUENCE: 5
agggtatctg ggctctgg                                           18

<210> SEQ ID NO 6
<211> LENGTH: 21
<212> TYPE: DNA
<213> ORGANISM: Artificial
<220> FEATURE:
<223> OTHER INFORMATION: Synthetic construct

<400> SEQUENCE: 6
ggctgaaaag ctcccgatta t                                       21
```

METHOD AND KIT FOR THE QUANTIFICATION OF NUCLEIC ACIDS

CROSS REFERENCE TO RELATED APPLICATIONS

This application is a National Stage of International Application No. PCT/KR2011/008494 filed Nov. 9, 2011, claiming priority based on Korean Patent Application No. 10-2010-0118387 filed Nov. 25, 2010, the contents of all of which are incorporated herein by reference in their entirety.

TECHNICAL FIELD

The present invention relates to the quantification of nucleic acids. More particularly, the present invention relates to a method and a kit for quantitatively analyzing nucleic acids, particularly, a trace amount of nucleic acid, for example, host cell DNA impurities, using a real-time polymerase chain reaction (hereinafter referred to as "real-time PCR") with random primers.

BACKGROUND ART

Accurate quantification of DNA is a starting point for guaranteeing quality in molecular biological applications most of which mainly analyze DNA. Quantification of trace amounts of DNA is of special importance in certain analytical applications in which the concentration of a target DNA is very low or only limited amounts of samples are available for analysis. Within this category are forensic DNA analysis, the detection and quantification of pathogenic agents, and the quantification of residual DNA impurities in biopharmaceutical products. Due to technical difficulties concerning quantification of trace-level DNA, special guidelines are often suggested to minimize analytical uncertainties and achieve a standard of best practice for the quantification of trace-level DNA. For example, the Food and Drug Administration (FDA) guidelines suggest that the acceptable residual amount of host cell DNA in biopharmaceutical drugs should be below 100 pg/dose, while the acceptable limit of host cell DNA allowed by the World Health Organization (WHO) and the European Union (EU) is up to 10 ng/dose.

Many different methods for quantifying DNA have been developed and applied for specific uses. UV spectrophotometry reading absorbance at 260 nm is the most common laboratory approach for quantifying DNA. However, it is hard to achieve the very high sensitivity required when quantifying practical samples containing only trace amounts of DNA. In addition, contamination by nucleotides, RNA, and proteins significantly interferes with the UV absorbance-based quantification of DNA. Fluorescence-based techniques are also widely used to quantify DNA. Given proper calibration standards, these methods show much higher sensitivity and accuracy compared with using UV spectrophotometry to quantify DNA. However, the fluorescence-based methods are also subject to interference by contaminants, and have been reported to be ineffective for quantifying amounts of DNA samples of less than 4 pg.

Several other methods were developed for a specific purpose regarding the quantification of an extremely low level DNA, especially for the quantification of residual host cell DNA in biopharmaceuticals. The hybridization method relies on radio isotopic or chemiluminescent detection of DNA hybridized to random and sequence-specific probes. Another method known as the 'threshold method' utilizes antibody-mediated detection and quantification of DNA captured by single-strand binding protein (SSB). Both the hybridization method and the threshold method are sufficiently sensitive to quantify picogram levels of DNA. These methods are advantageous in that they can quantify DNA in a sequence-independent manner and are applicable to universal DNA species. However, they also have disadvantageous including a relatively long analysis time, labor-intensiveness, and complicated procedures.

Another common platform for analyzing a trace amount of DNA is PCR, especially real-time PCR. Thanks to its extreme sensitivity and simplicity of experimentation, PCR technology has become the first choice for both qualitative and quantitative analysis of DNA in the lab. Although sequence-specificity is an incomparable merit of PCR technology, it also involves several important limitations with regard to the quantitative analysis of DNA. PCR will amplify and quantify only a specific target DNA, and not the whole DNA content. The quantity of the entirety of the DNA content therefore cannot be measured directly by PCR, but can only be estimated indirectly from the quantity of a specific target DNA. The sequence-specificity of PCR also limits the applicability of the method only to DNA samples containing more than one genome-equivalent amounts. The amount of human genomic DNA which allows individual genes to exist as at least one copy corresponds to 3 pg. Thus, even if the most effective reaction is performed under conditions ideal for PCR, the quantification limit by ordinary PCR will be 3 pg or above for human genomic DNA. When its performance is taken into consideration, ordinary PCR has a quantification limit of tens of picograms of mammalian genomic DNA. PCR is sensitive enough to allow the quantification of femtogram amounts of DNA from viruses and bacteria, but not sensitive enough to sufficiently quantify the DNA from mammalian cells. New approaches to amplifying multi-copy genes such as rDNA genes and Alu repeats have been applied to overcome the limited sensitivity of ordinary PCR with respect to mammalian cells. However, the approaches still have limitations because they are based on the assumption that the whole genome amount is distributed in a non-biased manner and a target multi-copy gene has a consistent copy number over the whole genome, which is impossible to achieve under ordinary analysis conditions. Conventional quantification technologies for trace amounts of DNA are summarized in Table 1, below.

TABLE 1

|  | Hybridization | Threshold | PCR |
| --- | --- | --- | --- |
| Specificity | Random sequence Species specific | Sing stranded DNA, Non-species specificity | Target sequence specific |
| Minimal detection length(bp) | 50 | 600 | 150 |
| Resistance to interference | ++ | + | + |
| Time | 48 | 6 | 2 |
| Sensitivity | 6 pg | 3 pg | <1 pg |

(source [T. Wolter, A. Richter, Assays for controlling host cell impurities in biopharmaceuticals, *Bioprocess Int.* 3 (2005) 40-46])

Therefore, it is very important to develop a sensitive and universal method for quantification of femtogram levels of DNA.

DISCLOSURE

Technical Problem

Leading to the present invention, intensive and thorough research into the accurate quantification of DNA, conducted by the present inventors, resulted in the finding that when combined with random primers, real-time PCR, which has been used to determine the quantity of a target gene on the basis of sequence specificity, allows nucleic acids, even if present in trance amounts, particularly, in sub-genomic amounts, to be quantified with high sensitivity and accuracy.

It is therefore an object of the present invention to provide a method for quantifying trace amounts of nucleic acids, particularly, host cell nucleic acid impurities.

It is another object of the present invention to provide a kit for quantification of trace amounts of nucleic acid, particularly, host cell nucleic acid impurities.

Technical Solution

In order to accomplish the above object, the present invention provide a method for quantifying a nucleic acid, comprising: performing a real-time polymerase chain reaction (PCR) on a target nucleic acid with a random primer; and determining an amount of the target nucleic acid from the result of the real-time PCR on a basis of correlation between a known amount of a reference nucleic acid and a result of real-time PCR for the reference nucleic acid.

Also, the present invention provides a kit for quantifying a nucleic acid, applicable to the method of the present invention, comprising: a reference nucleic acid, the amount of which is known; and a random primer.

Advantageous Effects

Combined with random primers, the method of the present invention can quantify sub-genomic amounts of nucleic acids with high precision and accuracy. Therefore, the present invention is applicable for use in the analysis of a forensic sample or nucleic acid impurities in biopharmaceuticals.

BEST MODE

Figure 1:
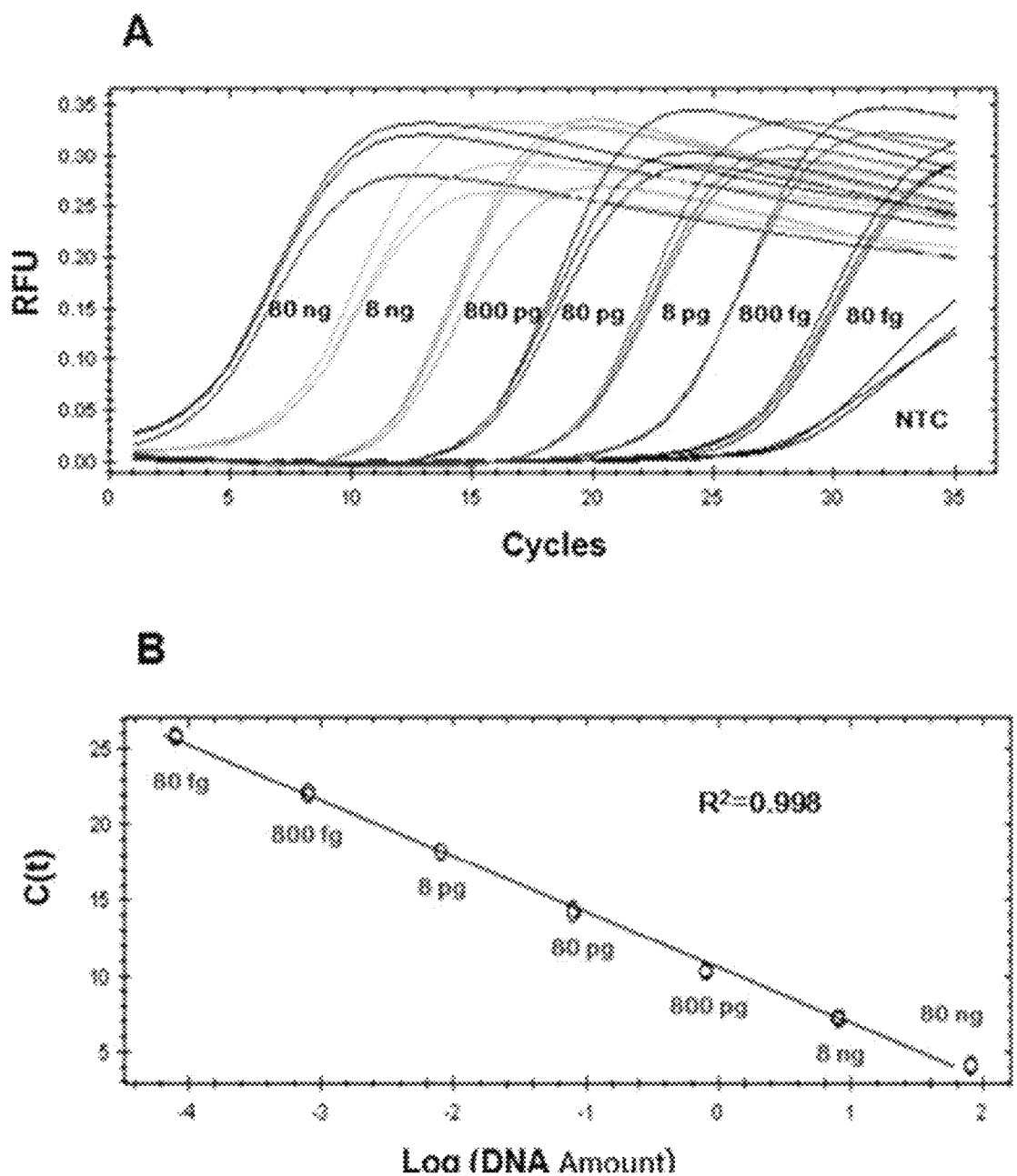
FIG. 1 is of amplification profiles of real-time DOP-PCR for HPD, CTD, HSD and λ DNA and related standard curve.

As used herein, the term "a trace amount of nucleic acids" is intended to refer to up to 1 pg of nucleic acids and the term "an extremely trace amount of nucleic acids" to up to 3 pg of nucleic acids.

The term "nucleic acid," as used herein, is intended to refer to a target to be quantified and encompasses not only DNA, for example, genomic DNA, but also RNA. In the latter case, the target to be quantified may be reverse transcribed into cDNA suitable for use in analysis by real-time PCR.

The term "random primer," as used herein, refers to a primer containing a random base sequence therein, and is intended to encompass all primers whether they consist partially or wholly of random base sequences.

Based on the new and surprising finding real-time PCR with random primers allows sub-genomic amounts of nucleic acids to be quantified with high precision and accuracy, the present inventors suggest the use of the present invention.

The present invention is characterized by the employment of random primers for real-time PCR so that real-time PCR is performed in a sequence non-specific manner rather than on the basis of sequence specificity. In addition, the present invention is characterized in that real-time PCR is used to quantify the total amount of nucleic acid, but not a specific region of a gene. Combined with random primers, the real-time PCR method of the present invention sequence can quantify a sub-genomic amount of DNA through non-specific amplification.

In accordance with an aspect thereof, the present invention provides a method for quantifying nucleic acid, comprising performing a real-time polymerase chain reaction (PCR) on a target nucleic acid with a random primer, and determining a level of the target nucleic acid from the result of the real-time PCR on a basis of correlation between a known amount of a reference nucleic acid and a result of real-time PCR for the reference nucleic acid. For example, $C_t$ (threshold cycle) values of real-time PCR can be used to determine an amount of the target nucleic acid.

According to one embodiment of the present invention, the target nucleic acid is present in a sub-genomic amount.

The target nucleic acid may range in amount from, for example, 80 fg to 8 ng.

In one embodiment of the present invention, target nucleic acids to be quantified are host cell nucleic acid impurities.

The real-time PCR employing random primer, useful in the present invention, is preferably real-time degenerate oligonucleotide primed PCR (DOP-PCR, Roche). A DOP-PCR strategy enables amplification of the entire genome of a DNA sample regardless of its origin and sequence (Telenius, H. et al. (1992), Cytogenetic analysis by chromosome painting using dop-per amplified flow-sorted chromosomes. Genes, Chromosomes and Cancer, 4:257-263). Over ordinary PCR targeting specific genes, the real-time DOP PCR has two potential advantages: sequence independency, and potential sensitivity that is not limited by the requirements for one gemone-equivalent amount of DNA as a template. Theoretically, DOP-PCR could successfully produce amplicons from a sub-genomic amount of DNA even if the sequences and origins of the target DNA are not known. In the real-time DOP-PCR method according to the present invention, for example, primers of SEQ ID NO. 1 (CCGACTC-GAGNNNNNNATGTGG, anchoring sequence underlined), SEQ ID NO. 2 (CCGACTCGAGNNNNNNATTTCG), SEQ ID NO. 3 (CCGACTCGAGNNNNNNCGGGTC), and SEQ ID NO. 4 (CCGACTCGAGNNNNNNTGTTCG), which are different from each other in anchoring sequence, are employed alone or in combination.

When applied to the human placental DNA the amount of which was accurately determined, the PCR method was found to allow for the accurate and stable quantification of DNA samples ranging from 80 fg to 8 ng, with the limit of determination (LOD) given to 80 fg. In addition, the PCR method of the present invention provided a measurement accuracy of 5% with an analytical precision of 15% for 4 pg of a DNA sample, which are too high for specific DNA amplification or a picogreen method to achieve.

In accordance with another aspect thereof, the present invention provides a kit for the quantification of nucleic acids using real-time PCR with random primers. The kit may comprise a known amount of a nucleic acid, and a random primer. Optionally, the kit may further comprise a common mixture used for ordinary real-time PCR, for example, a DNA polymerase (e.g., Taq polymerase), a buffer, and a fluorescent dye (e.g., SYBR). The real-time PCR mixture may be prepared on the basis of, for example, SYBR premix EX Taq™ (Takara).

With reference to a proper standard DNA, the potential of the method and kit according to the present invention to be robustly applied to the analyses of trace amounts of forensic DNA samples and residual DNA impurities in biopharmaceuticals is expected to be strong.

Mode for Invention

A better understanding of the present invention may be obtained from the following examples which are set forth to illustrate, but are not to be construed as limiting the present invention.

Example 1

Assay for Validity of Real-Time DOP-PCR

Human placenta DNA (HPD) (Sigma St. Louis, Mo.) was fragmented by sonication to sizes ranging from 1 to 5 kb and quantified by ICP-OES (Inductively Coupled Plasma-Optical Emission Spectrometer). Calibration standards for real-time PCR were prepared by gravimetric fold serial dilutions of ICP-OES-quantified HPD. Test samples were also prepared by gravimetric dilutions of the same HPD. Concentrations of calf thymus DNA (CTD, Sigma), herring sperm DNA (HSD, Sigma) and λ DNA (Fermentas) were determined by measuring UV absorbance at 260 nm. Concentration ratios of the DNA samples to the HPD were CTD:HSD:λ DNA=4.4:7.8: 0.5. These values were calibrated for the known amount of HPD. The HPD fragments were single or double cut with HPD Alu I and/or Hinf I restriction enzyme (GE healthcare) into DNA samples 500-1500 bp long.

A degenerate oligonucleotide primer (5'-CCGACTC-GAGNNNNNNATGTGG-3'; SEQ ID NO:1) was synthesized (Genotech, Daejeon, Korea). All real-time PCR mixtures were prepared based on SYBR premix EX Taq™ (Takara). The reaction mixture contained 2 µM of the primer and 80 fg-80 ng of genomic DNA. Real-time DOP-PCR was performed in a final reaction volume of 15 µL using Miniopticon™ instrument (Bio-rad, Hercules, Calif.) equipped with CFX Manager™ V1.5 software (Bio-rad, Hercules, Calif.). The real-time DOP-PCR was performed following a modified procedure. In brief, the PCR started with initial denaturation for 10 minutes at 95° C., and was carried out with five low stringency cycles of 94° C. for 60 seconds, 32° C. for 90 seconds, and 72° C. over a 3-minute period, and then with 35 high stringency cycles of 94° C. for 1 min, 62° C. for 1 min and 72° C. for 2 min, followed by the final extension at 72° C. for 7 min.

The validity of the real-time DOP-PCR was examined using four different genomic DNA samples ranging from 80 fg to 80 ng. To determine the concentration of a unknown sample, the genomic DNA was subjected to 10-fold serial dilution to construct a standard curve. Although DOP-PCR amplified a high diversity of amplicons, all amplification profiles were observed to be similar to those of typical PCR for specific genes. In the profiles, there were regular intervals of $C_t$ (threshold cycles) between DNA samples 10-fold diluted from 800 fg to 8 ng, irrespective of DNA species. All standard curves constructed were observed to exhibit a good linearity for diverse DNA species as proven by the $R^2$ values of approximately 1, indicating that the real-time DOP-PCR method guarantees high accuracy and validity in the DNA concentration range.

Linear regression of the $C_t$ values and genomic DNA amounts showed negative linearity (slope=−4.1, −3.7, or −4.2) corresponding to a PCR efficiency of 75%, 86% and 73%, respectively. The optimal efficiency (100%) corresponds to a slope value of −3.31, reflecting the doubling of the amplicons in each cycle. The amplification efficiency based on the random primers was between 73% and 86% whereas typical PCR analysis is reported to have an amplification efficiency of from 90% to 110%.

FIG. 1 shows amplification profiles of real-time DOP-PCR for standard HPD (A) and a standard curve obtained therefrom (B).

Figure 2:
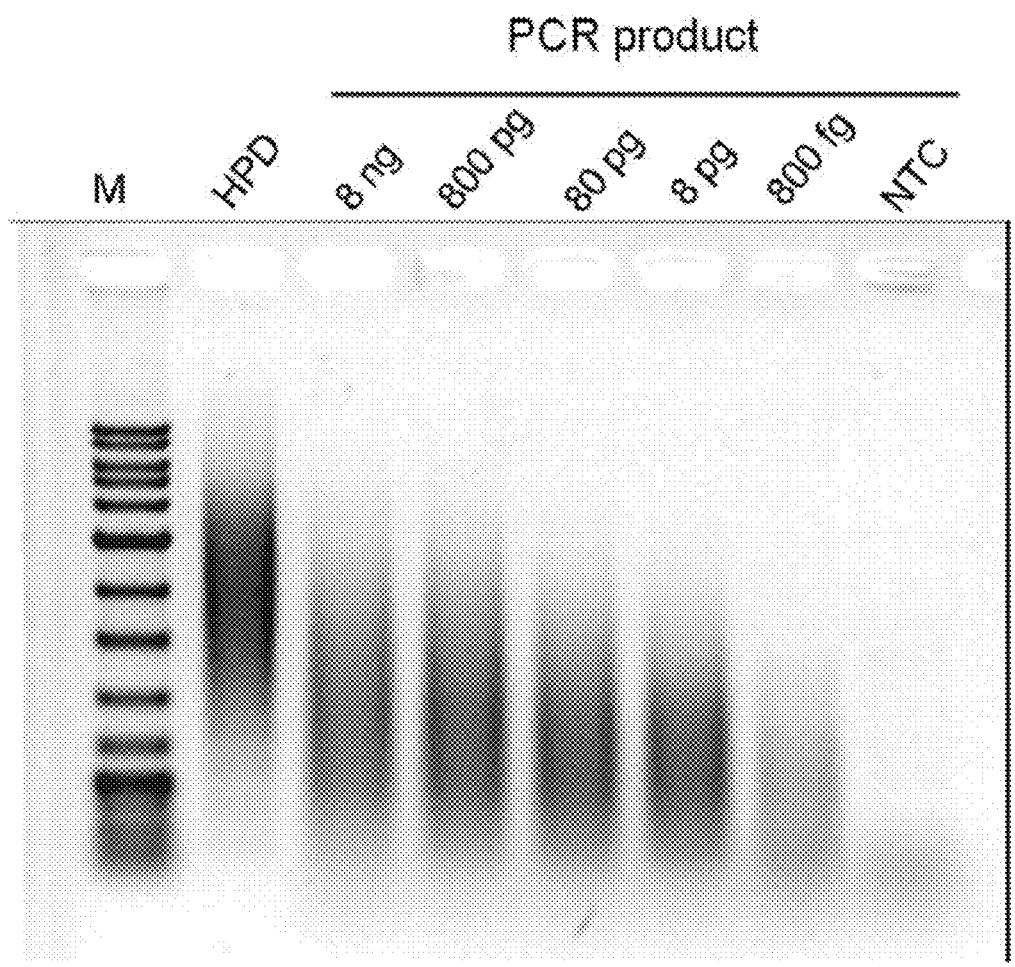
FIG. 2 is a photograph showing agarose gel electrophoresis results of DOP-PCR products for HPD.

FIG. 2 shows agarose gel electrophoresis results of the template HPD (lane 2), amplicons (lanes 3-7) and NTC (no-template control, lane 8). HPD fragments 1-5 kb long were used as templates. The amplicons of used gemonic DNA were detected at 0.1 to 3 kb, with a smear intensity of from 0.25 to 1 kb.

Example 2

Quantification of Unknown DNA Sample

To demonstrate the precision and reliability of the quantitative real-time PCR using random primers within a valid range, two DNA quantification methods, a PicoGreen assay and quantitative real-time PCR analysis using specific primers were employed for comparison.

For use in quantifying human genomic DNA, primers were designed to contain an STR (Short Tandem Repeat) sequence of the human tyrosine hydroxylate (TH01) gene, which is widely used as a forensic DNA. The sequence of TH01 located in chromosome 11(11p15.5) was derived from the GenBank locus AF536811. Specific primers for the amplification of the TH01 locus were synthesized (Genotech, Daejeon, Korea): F: 5'-AGGGTATCTGGGCTCTGG-3'; SEQ ID NO: 5; and R: 5'-GGCTGAAAAGCTCCCGATTAT-3'; SEQ ID NO: 6. The TH01 locus was amplified under the following conditions: initial denaturation at 95° C. for 3 min, followed by 35 cycles of 94° C. for 5 sec and 60° C. for 34 sec.

An amplicon obtained from the HPD was 180 bp long. The PCR product obtained when using specific primers appeared as a sharp band on agarose gel and as a single peak in a melting point curve, with an amplification efficiency of from 86.6% to 100.9%. Fluorescence of the PCR products was monitored during amplification, with SYBR Green I used as an intercalating dye for both random and specific primer-based analysis. An alternative quantification method is a PicoGreen assay, which is reported to have high fluorescence sensitive capability of detecting as low as 250 pg/mL double-stranded DNA.

Figure 3:
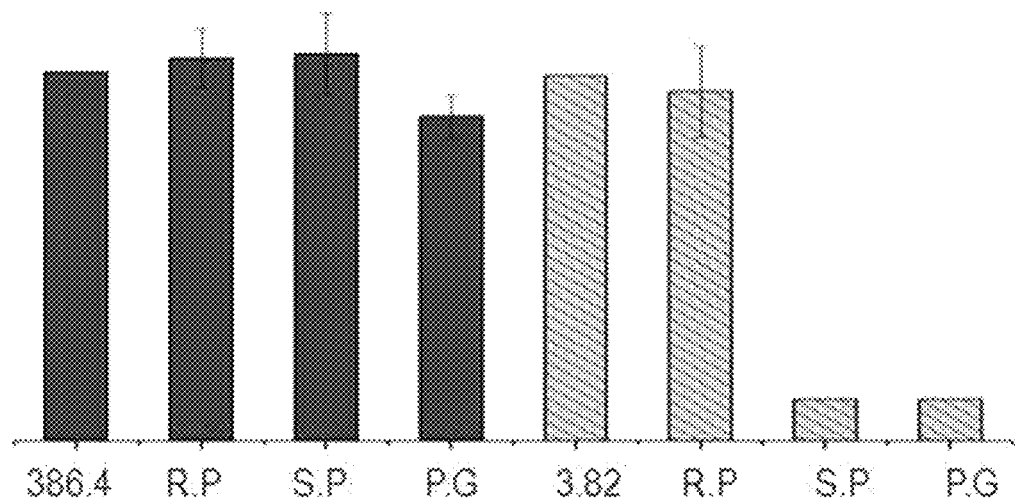
FIG. 3 is a graph showing DNA concentrations as measured by quantitative real-time PCR and PicoGreen Assay (P.G) using random primers (R.P) or specific primers (S.P)

Table 2 summarizes statistics of the concentrations. FIG. 3 shows DNA concentrations as measured by quantitative real-time PCR and a PicoGreen Assay (P.G) using random primers (R.P) or specific primers (S.P).

TABLE 2

| Measurement Type | Expected (pg/µL) | Measured (pg/µL) | S.D. (pg/µL) | Precision (%) | Accuracy (%) |
|---|---|---|---|---|---|
| R.P | 386.4 | 402.8 | 35.1 | 8.7 | 4.2 |
| S.P | 386.4 | 407.6 | 48.9 | 12.0 | 5.5 |
| P.G | 386.4 | 333.7 | 25.6 | 7.7 | −13.6 |

TABLE 2-continued

| Measurement Type | Expected (pg/μL) | Measured (pg/μL) | S.D. (pg/μL) | Precision (%) | Accuracy (%) |
|---|---|---|---|---|---|
| R.P | 3.82 | 3.63 | 0.54 | 14.9 | −5.0 |
| S.P | 3.82 | N/A | N/A | N/A | N/A |
| P.G | 3.82 | N/A | N/A | N/A | N/A |

DNA concentrations were expected to be 386.4 and 3.82 pg/μL for R.P, S.P and P.G. Measurements of average DNA concentrations were 402.8 pg/μL and 407.6 pg/μL for R.P and S.P, respectively, both of which were higher than the expected values. In contrast, the average DNA concentration for P.G was measured at 333.7 pg/μL, which was even lower than the expected value. Of the three, accordingly, DNA quantification with R.P guaranteed the most precise values.

As stated above, it was possible for all three of the quantification methods to determine approximately 400 pg/μL whereas only the random primer method could be used to determine the concentration of 3.8 pg/μL.

Amplification of a certain region of a gene, especially a single-copy gene, requires at least 7 copies of the gene as a template for PCR. One copy of the haploid nucleus corresponds to 3.3 pg of human genomic DNA. The limit of determination by DNA quantification with specific primers is estimated to be 80 pg/μL, which corresponds to 24 copies of human genomic DNA. Therefore, it is impossible to apply ordinary PCR methods with specific primers to the amplification of 8 pg/μL DNA, that is, 2.4 copies of DNA. In order to overcome the limited sensitivity of ordinary PCR, new approaches of amplifying multi-copy genes such as Alu, rDNA, mtDNA, etc. have been introduced into the quantification analysis. However, these target genes vary depending on cells and individuals, so that the multi-copy PCR methods cannot promise accurate quantification results.

For a final sensitivity of approximately 50 pg dsDNA per sample, a PicoGreen assay is reported to have a sensitivity of 25 pg/mL dsDNA in a volume of 2 mL or 250 pg/mL dsDNA in a volume of 200 μL. In order to achieve a detection sensitivity of 800 pg/mL dsDNA, therefore, the PicoGreen assay requires a volume of 62.5 μL containing a total DNA amount of 50 pg. In contrast, the random primer-based quantitative real-time PCR requires only 1 μL of a DNA solution with a concentration of 800 pg/mL, demonstrating that the quantitative real-time PCR can provide accurate data for unknown samples within the detection limit.

Figure 4:
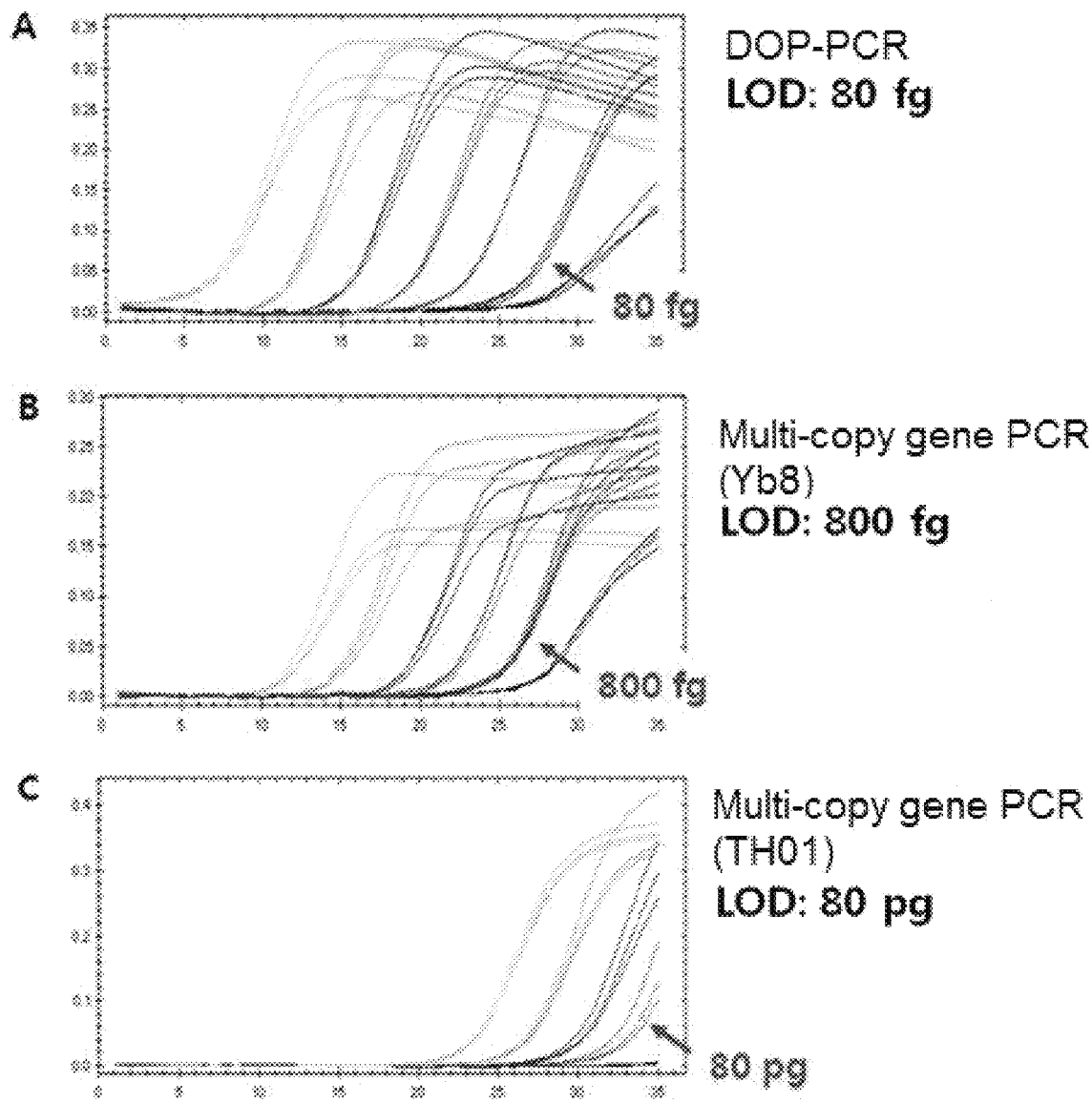
FIG. 4 is of amplification profiles showing quantification performances of real-time DOP-PCR, PCR for multi-copy gene, and PCR for single copy gene.

FIG. 4 shows quantification performances of various PCR approaches including real-time DOP-PCR (A), PCR for multi-copy gene (Yb8) (B), and PCR for single copy gene (TH01) (C). As can be seen in FIG. 4, the nucleic acid quantification limit of the DOP-PCR according to the present invention was found to be 80 fg whereas the limits of detection by PCR for a single copy gene and for a multi-copy gene are 80 pg and 800 fg, respectively.

Example 3

Quantification Performance of Real-Time DOP-PCR Depending on Anchoring Sequence

Figure 5:
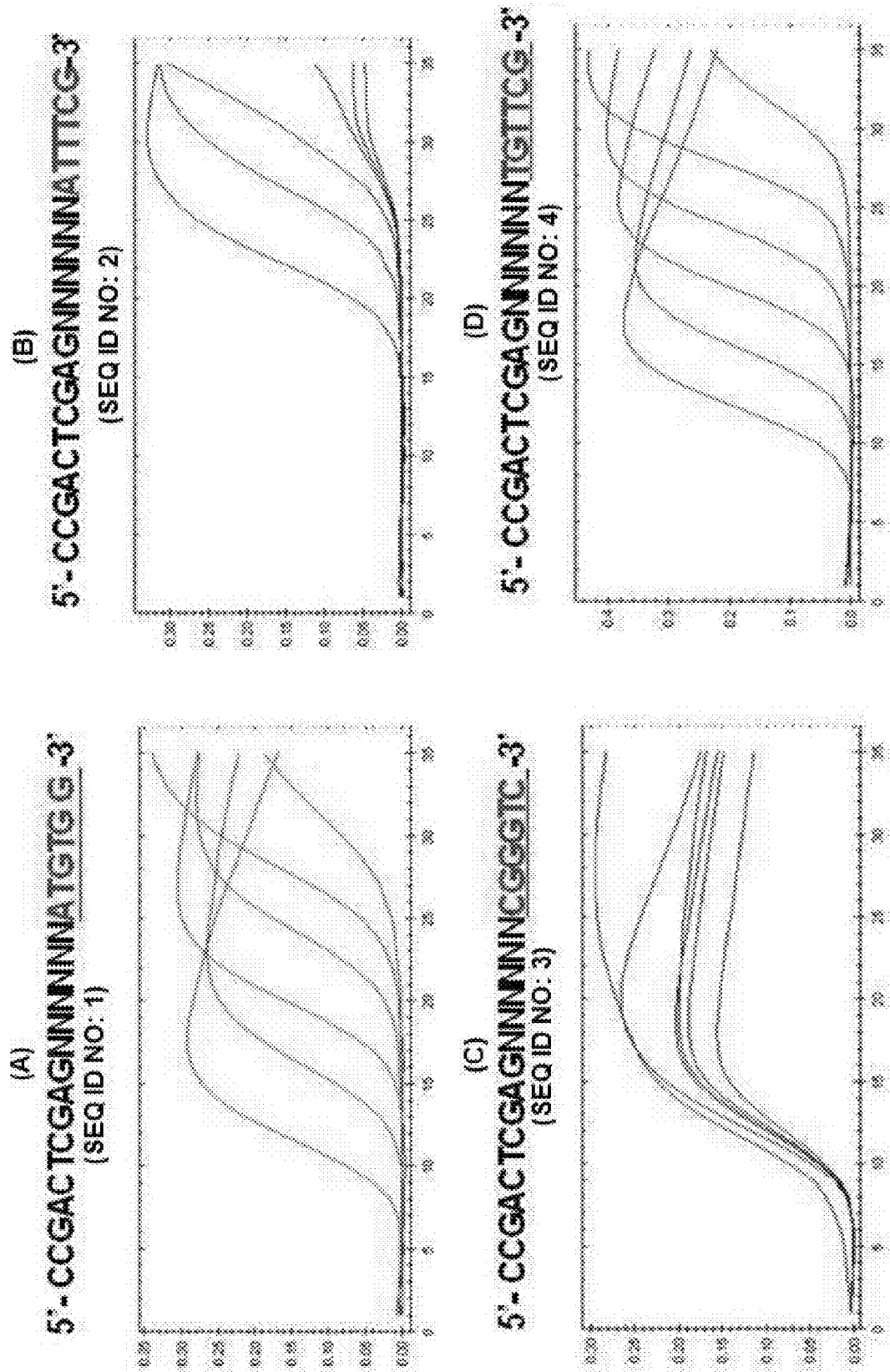
FIG. 5 is of amplification profiles showing quantification performances of real-time DOP-PCR depending on anchoring sequences.

The anchoring sequence in the primer of SEQ ID NO: 1 prepared in Example 1 was modified to synthesize primers of SEQ ID NOS: 2 to 4 which were used for real-time DOP-PCR. FIG. 5 shows profiles of real-time DOP-PCR for the standard material HPD. As shown in FIG. 5, the amplification profiles Show different efficiencies depending on anchoring sequences in the DOP primers. Two primers with anchoring sequences of 50% GC contents exhibited proportionate and sensitive amplification profiles, while insensitive or non-discriminating amplification profiles were obtained by uses of primers of 40% and 80% GC contents, respectively.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

SEQUENCE LIST TEXT

SEQ ID NO: 1 is a degenerate oligonucleotide primer.
SEQ ID NO: 2 is a primer modified at the anchoring sequence of the primer of SEQ ID NO: 1.
SEQ ID NO: 3 is a primer modified at the anchoring sequence of the primer of SEQ ID NO: 1.
SEQ ID NO: 4 is a primer modified at the anchoring sequence of the primer of SEQ ID NO: 1.
SEQ ID NO: 5 is a forward primer for amplification of TH01 locus.
SEQ ID NO: 6 is a reverse primer for amplification of TH01 locus.

The invention claimed is:

1. A method for quantifying a nucleic acid, comprising:
performing a real-time polymerase chain reaction (PCR) on a target nucleic acid with a primer selected from the group consisting of primers of SEQ ID NOS: 2 to 4 and a combination thereof; and
determining an amount of the target nucleic acid from results of the real-time PCR on a basis of a correlation between a known amount of a reference nucleic acid and a result of real-time PCR for the reference nucleic acid,
wherein the real-time PCR is real-time degenerated oligonucleotide primed PCR.

2. The method of claim 1, wherein the target nucleic acid is present in a sub-genomic amount.

3. The method of claim 1, wherein the target nucleic acid is present in an amount of from 80 fg to 8 ng.

4. The method of claim 1, wherein the target nucleic acid is a genomic DNA or a cDNA synthesized by reverse transcription from RNA.

5. The method of claim 1, wherein the target nucleic acid is a host cell nucleic acid impurity.

6. The method of claim 1, being applicable for use in analysis of a forensic sample or a nucleic acid impurity in biopharmaceuticals.

7. The method of claim 1, wherein the determining step is carried out using $C_t$ (threshold cycle) values of real-time PCR.

* * * * *